United States Patent [19]  [11] 4,111,942
Lee et al.  [45] Sep. 5, 1978

[54] 10-AMINO-5H-[1]BENZOPYRANO[4,3-c]PYRIDINES

[75] Inventors: Cheuk Man Lee, Libertyville; Harold Elmer Zaugg, Lake Forest, both of Ill.

[73] Assignee: Abbott Laboratories, North Chicago, Ill.

[21] Appl. No.: 781,903

[22] Filed: Mar. 28, 1977

[51] Int. Cl.² .................................. C07D 405/14
[52] U.S. Cl. .................. 260/293.58; 260/294.8 B; 260/295 T; 260/296 H; 260/297 T; 544/284
[58] Field of Search ........ 260/293.58, 295 T, 294.8 B, 260/296 H

[56] References Cited
U.S. PATENT DOCUMENTS 3,654,312  4/1972  Pars et al. ........................ 260/293.58
3,878,219  4/1975  Lee ................................. 260/295 T Primary Examiner—Henry R. Jiles
Assistant Examiner—Richard A. Schwartz
Attorney, Agent, or Firm—Gildo E. Fato; Robert L. Niblack

[57] ABSTRACT

This invention provides compounds of the structure

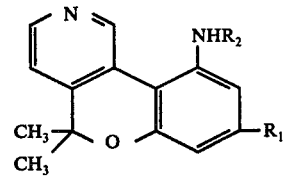

where $R_1$ is $C_3$–$C_{20}$ alkyl or arylalkyl; $R_2$ is hydrogen, loweralkanoyl, loweralkylsulfonyl, loweralkoxycarbonyl, carbamoyl or

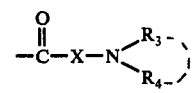

wherein X is an alkylene group having from 2 to 4 carbon atoms; and $R_3$ and $R_4$ are the same or different members of the group consisting of hydrogen or loweralkyl, or $R_3$ and $R_4$ taken together form a 5-, 6-, or 7-member heterocyclic ring; and the pharmaceutically acceptable acid addition salts thereof.

The compounds of this invention are useful as analgesics, tranquilizers and sedative-hypnotics.

9 Claims, No Drawings

10-AMINO-5H-[1]BENZOPYRANO[4,3-C]PYRIDINES

Detailed Description of the Invention

This invention relates to pyridines, and more particularly to 10-amino-5H-[1]benzopyrano[4,3-c]pyridines which are useful as analgesics, tranquilizers and sedative-hypnotics.

According to one aspect of the subject invention there is provided novel pyridine derivatives of the formula

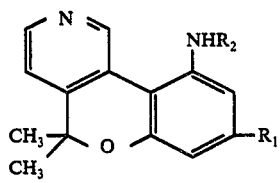

where $R_1$ is $C_3$—$C_{20}$ alkyl or arylalkyl; $R_2$ is hydrogen, loweralkanoyl, loweralkylsulfonyl, loweralkoxycarbonyl, carbamoyl or

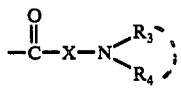

wherein X is an alkylene group having from 2 to 4 carbon atoms; and $R_3$ and $R_4$ are the same or different members of the group consisting of hydrogen or loweralkyl, or $R_3$ and $R_4$ taken together form a 5-, 6-, or 7-member heterocyclic ring; and the acid addition salts thereof.

The term "$C_3$–$C_{20}$ alkyl" as used herein, refers to both straight and branched chain alkyl radicals including n-propyl, iso-propyl, n-butyl, sec-butyl, tertiary-butyl, n-pentyl, n-hexyl, 2-heptyl, n-heptyl, 3-methyl-2-octyl, n-octyl, n-nonyl, 2-tetradecyl, 2-eicosanyl, and the like.

The term "arylalkyl" refers to an alkyl group of 1 to 10 carbon atoms where one of the hydrogen atoms of the alkyl group is substituted by phenyl or a substituted phenyl.

As used herein, the term "loweralkanoyl" means saturated, monovalent, aliphatic radicals, derived from a monocarboxylic acid, including straight or branched chain radicals of from one to six carbon atoms, as illustrated by, but not limited to formyl, acetyl, propionyl, α-methylpropionyl, butyryl, hexanoyl, and the like.

The term "loweralkyl" refers to $C_1$ to $C_6$ alkyl groups including methyl, ethyl, n-propyl, iso-propyl, n-butyl, sec-butyl, tertiary-butyl, n-pentyl, iso-pentyl, neo-pentyl, n-hexyl and the like.

The compounds of this invention exhibit activity as analgesics, tranquilizers and sedative-hypnotics. The analgesic activity is obtained at dosages of from 1 to 10 mg./kg. of body weight orally and from 0.2 to 5.0 mg./kg. of body weight interperitoneally (i.p.). Similarly, the tranquilizing activity is obtained at dosages of from 1.5 to 15.0 mg./kg. of body weight orally and from 0.5 to 5.0 mg./kg. of body weight interperitoneally (i.p.).

The present compounds may be prepared by means of a variety of techniques. For example, the compounds can be prepared, as illustrated below in Scheme A, by first alkylating an 8-substituted-10-hydroxy-5,5-dimethyl-5H-[1]benzopyrano [4,3-c]pyridine (I) with 4-chloro-2-phenylquinazoline and sodium hydride in dimethylformamide to provide a 4-aryloxy-2-phenylquinazoline (II) which is heated at approximately 330° C. to give 3-aryl-2-phenyl-4(3H)quinazolinone (III). Then, the quinazolinone (III) is hydrolyzed with potassium hydroxide in ethylene glycol to provide an 8-substituted-10-amino-5,5-dimethyl-5H-[1]benzopyrano[4,3-c]pyridine (IV). This pyridine (IV) is then reacted with appropriate reagents to yield 10-substituted-amino derivatives of this invention.

The compounds are prepared according to the following reaction scheme:

SCHEME A

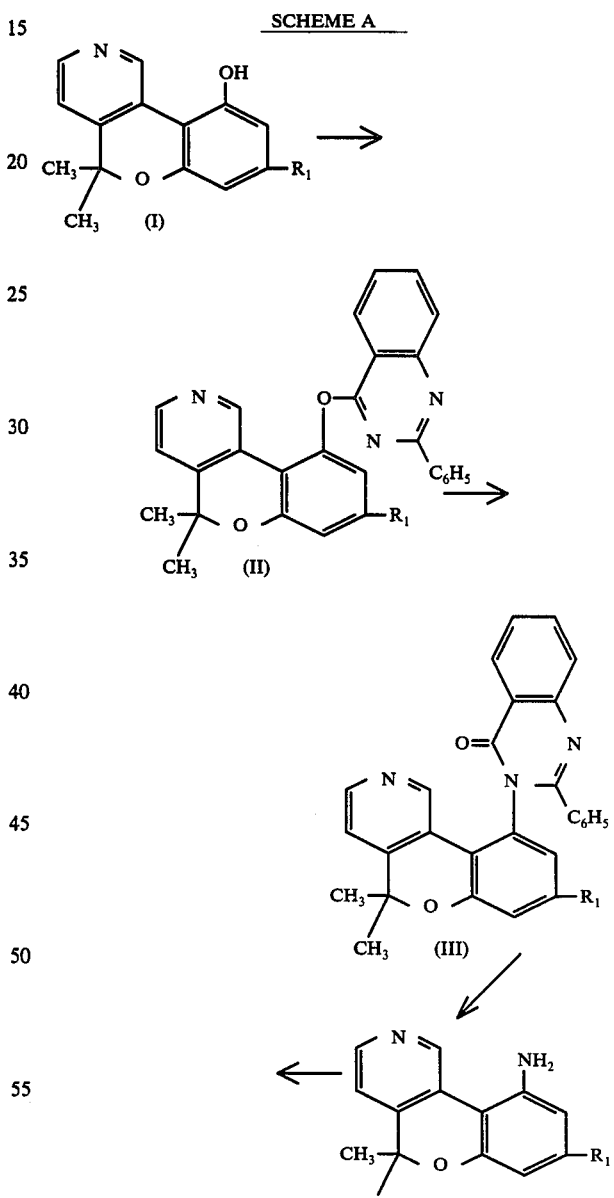

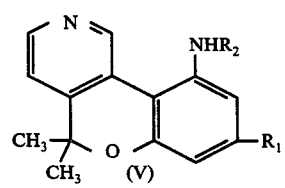

3

The compounds that may be produced according to the above illustrated method include:

| VI | 10-Amino-5,5-dimethyl-8-(1,2-dimethylheptyl)-5H-[1]benzopyrano[4,3-c]pyridine; |
|---|---|
| VII | 10-Amino-8-[5-(4-fluorophenyl)-2-pentyl]-5,5-dimethyl-5H-[1]benzopyrano[4,3-c]pyridine maleate; |
| VIII | 10-Acetamido-5,5-dimethyl-8-(1,2-dimethylheptyl)-5H-[1]benzopyrano[4,3-c]pyridine; |
| IX | 8-[5-(4-Fluorophenyl)-2-pentyl]-5,5-dimethyl-10-(methylsulfonamido)-5H-[1]benzopyrano[4,3-c]pyridine; |
| X | 10-(Carbethoxyamino)-8-[5-(4-fluorophenyl)-2-pentyl]-5,5-dimethyl-5H-[1]benzopyrano[4,3-c]pyridine; |
| XI | 8-[5-(4-Fluorophenyl)-2-pentyl]-5,5-dimethyl 10-ureido-5H-[1]benzopyrano[4,3-c]pyridine; |
| XII | 5,5-Dimethyl-8-(1,2-dimethylheptyl)-10-(4-piperidinobutyrylamino)-5H-[1]benzopyrano[4,3-c]pyridine hydrochloride; |
| XIII | 8-[5-(4-Fluorophenyl)-2-pentyl]-5,5-dimethyl-10-[4-(dimethylamino)butyrylamino]-5H-[1]benzopyrano[4,3-c]pyridine hydrochloride |

The following examples are presented to further illustrate the present invention.

EXAMPLE 1

10-Amino-5,5-dimethyl-8-(1,2-dimethylheptyl)-5H-[1]benzopyrano[4,3-c]pyridine (VI)

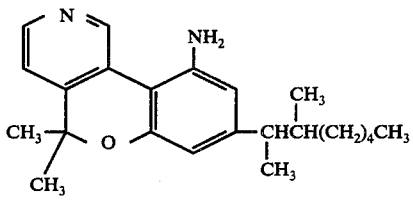

A solution of 7.07 g. (0.02 mole) of 10-hydroxy-5,5-dimethyl-8-(1,2-dimethylheptyl)-5H-[1]benzopyrano[4,3-c]-pyridine in 100 ml. of dimethylformamide was added to a stirred suspension of 1.06 g. (0.022 mole) of 50% sodium hydride (dispersed in mineral oil), in 20 ml. of dimethylformamide. The mixture was stirred at 80° C. for 1-½ hour and after cooling to room temperature, 4.8 g. (0.02 mole) of 4-chloro-2-phenylquinazoline was added. The mixture was stirred at 100° C. for 15 hours, and then at 150° C. for 4 hours. The cooled mixture was poured into water and extracted with ether. The combined ether extracts were washed with water, dried over anhydrous magnesium sulfate, and evaporated in vacuo. The residue was purified by chromatography on a Florisil (60–100 mesh) column using chloroform to give 7.5 g. of the O-alkylated product. The O-alkylated product was heated in a Woods' metal bath at 330° C. under nitrogen for 3 hours. The crude product was purified by chromatography on a Florisil column using graded chloroform-methanol mixtures to give 6.6 g. of the rearranged product. A mixture of 6.6 g. of the rearranged product and 60 g. of potassium hydroxide in 40 ml. of water and 800 ml. of ethylene glycol was stirred and heated at 150° C. for 18 hours. The mixture was diluted with water and extracted with ether. The ether extracts were washed with water, dried over anhydrous magnesium sulfate, and evaporated in vacuo. The residue was chromatographed on a Florisil column using chloroform to yield the pure product.

Analysis Calcd. for $C_{23}H_{32}N_2O$: C, 78.36; H, 9.15; N, 7.97 Found: C, 78.02; H, 9.23; N, 7.62

EXAMPLE 2

10-Amino-8-[5-(4-fluorophenyl)-2-pentyl]-5,5-dimethyl-5H-[1]benzopyano[4,3-c]pyridine maleate (VII)

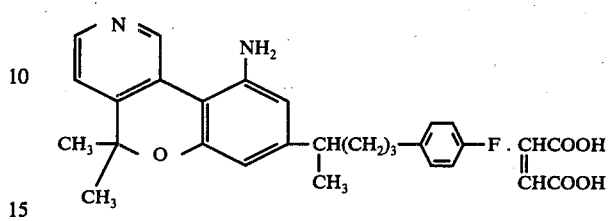

10-Amino-8-[5-(4-fluorophenyl-2-pentyl]-5,5-dimethyl-5H-[1]benzopyrano[4,3-c]pyridine maleate was prepared by converting 8-[5-(4-fluorophenyl)-2-pentyl]-10-hydroxy-5,5-dimethyl-5H-[1]benzopyrano[4,3-c]pyridine according to the method of Example 1. The O-alkylated product was purified by recrystallization from ethanol; m.p. 150–152°. The maleate salt was prepared by adding one equivalent of maleic acid in ether to the free base, and recrystallization from methylene chloride-ether; m.p. 117°–118°.

Analysis Calcd. for $C_{25}H_{27}FN_2O \cdot C_4H_4O_4$: C, 68.76; H, 6.17; N, 5.53 Found: C, 68.83; H, 6.19; N, 5.55.

EXAMPLE 3

10-Acetamido-5,5-dimethyl-8-(1,2-dimethylheptyl)5H-[1]benzopyrano[4,3-c]pyridine (VIII)

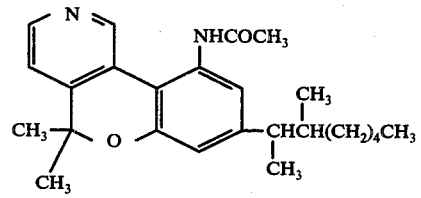

Acetyl chloride (0.39 g., 5 mmole) was added to a stirred solution of 0.78 g. (2.2 mmole) of 10-amino-5,5-dimethyl-8-(1,2-dimethylheptyl)-5H-[1]benzopyrano[4,3-c]-pyridine in 10 ml. of dry pyridine, cooled in an ice bath. After stirring at room temperature for 18 hours, the mixture was poured into 100 ml. of ice water and exracted with ether. The ether extracts were washed with water, dried over anhydrous magnesium sulfate, and evaporated in vacuo. The residue was purified by chromatography on a Florisil column (60–100 mesh) and eluted with chloroform and then graded chloroform-methanol mixtures to give the pure product.

Analysis Calcd. for $C_{25}H_{34}N_2O_2$: C, 76.10; H, 8.69; N, 7.10 Found: C, 75.05; H, 8.68; N, 6.93.

EXAMPLE 4

8-[5-(4-Fluorophenyl)-2-pentyl]-5,5-dimethyl-10-(methylsulfonamido)-5H-[1]benzopyrano[4,3-c]pyridine (IX)

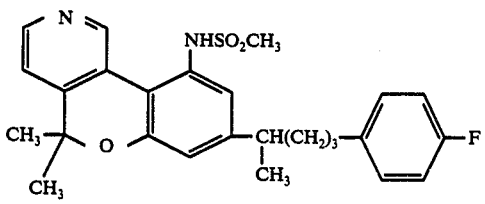

The titled compound was prepared by reacting 10-amino-8-[5-(4-fluorophenyl)-2-pentyl]-5,5-dimethyl-5H-[1]benzopyrano[4,3-c]pyridine with methanesulfonyl chloride according to the method of Example 3. The crude product was filtered and recrystallized from acetonitrile; m.p. 208°–209°.

Analysis Calcd. for $C_{26}H_{29}FN_2O_3S$: C, 66.64; H, 6.24; N, 5.98 Found: C, 67.17; H, 6.34; N, 6.08.

EXAMPLE 5

10-(Carbethoxyamino)-8-[5-(4-fluorophenyl)-2-pentyl]-5,5-dimethyl-5H-[1]benzopyrano[4,3-c]pyridine (X)

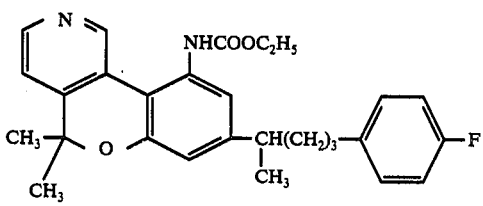

The title compound was prepared by reacting 10-amino-8-[5-(4-fluorophenyl)-2-pentyl]-5,5-dimethyl-5H-[1]benzopyrano[4,3-c]pyridine with ethyl chloroformate according to the method of Example 3.

Analysis Calcd. for $C_{28}H_{31}FN_2O_3$: C, 72.70; H, 6.76; N, 6.06 Found: C, 72.75; H, 6.82; N, 6.07.

EXAMPLE 6

8-[5-(4-Fluorophenyl)-2-pentyl]-5,5-dimethyl-10-ureido-5H-[1]benzopyrano[4,3-c]pyridine (XI)

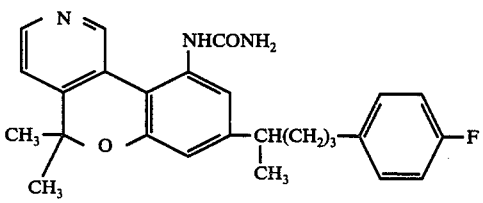

Potassium cyanate (1.22 g., 0.015 mole) was added to a stirred solution of 1.95 g. (0.005 mole) of 10-amino-8-[5-(4-fluorophenyl)-2-pentyl]-5,5-dimethyl-5H-[1]benzopyrano [4,3-c]pyridine in 20 ml. of glacial acetic acid. The mixture was stirred at room temperature for 18 hours and was diluted with 80 ml. of water. After cooling in an ice bath, the aqueous acetic acid solution was decanted, the residue was triturated with water, cooled, filtered, and recrystallized from acetonitrile, m.p. 179°–181°.

Analysis Calcd. for $C_{26}H_{28}FN_3O_2$: C, 72.03; H, 6.51; N, 9.69; Found: C, 72.36; H, 6.61; N, 9.62.

EXAMPLE 7

5,5-Dimethyl-8-(1,2-dimethylheptyl)-10-(4-piperidinobutyrylamino)-5H-[1]benzopyrano[4,3-c]pyridine hydrochloride (XII)

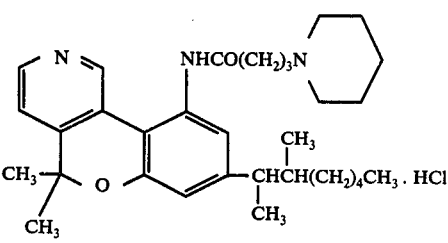

A mixture of 0.87 g. (2.47 mmole) of 10-amino-5,5-dimethyl-8-(1,2-dimethylheptyl)-5H-[1]benzopyrano[4,3-c]-pyridine, 0.51 g. (2.47 mmole) of 4-piperidinobutyric acid hydrochloride, 0.56 g. (2.72 mmole) of dicyclohexylcarbodiimide, and 50 ml. of dry methylene chloride was stirred at room temperature for 72 hours. The mixture was cooled and filtered and the filtrate concentrated to a residue which was recrystallized from methylene chloride-ether, m.p. 185–186°.

Analysis Calcd. for $C_{32}H_{47}N_3O_2.HCl.H_2O$: C, 68.60; H, 9.00; N, 7.50 Found: C, 68.79; H, 9.09; N, 7.59.

EXAMPLE 8

8-[5-(4-Fluorophenyl)-2-pentyl]-5,5-dimethyl 10-[4-(dimethylamino)butyrylamino]-5H-[1]benzopyrano[4,3-c]pyridine hydrochloride (XIII)

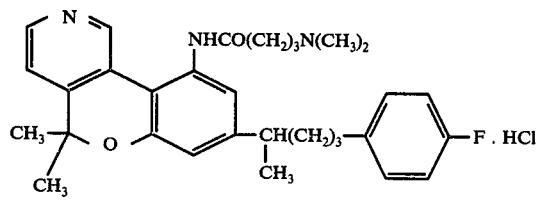

The titled compound was prepared according to the method of Example 7 by reacting equimolar quantities of 10-amino-8-[5-(4-fluorophenyl)-2-pentyl]-5,5-dimethyl-5H-[1]-benzopyrano[4,3-c]pyridine and 4-(dimethylamine)butyric acid hydrochloride in the presence of dicyclohexylcarbodiimide in methylene chloride.

We claim:
1. A compound represented by the formula

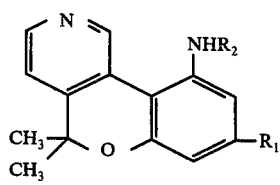

where $R_1$ is $C_3$–$C_{20}$ alkyl or halophenylloweralkyl; $R_2$ is hydrogen, loweralkanoyl, loweralkylsulfonyl, loweralkoxycarbonyl, carbamoyl or

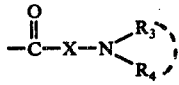

wherein X is an alkylene group having from 2 to 4 carbon atoms; and $R_3$ and $R_4$ are the same or different members of the group consisting of hydrogen or lower-alkyl; or $R_3$ and $R_4$ taken together form a 5-, 6-, or 7- member heterocyclic ring; and the pharmaceutically acceptable acid addition salts thereof.

2. A compound according to claim 1, wherein $R_2$ is H and $R_1$ is

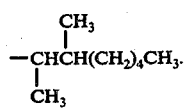

3. A compound according to claim 1, wherein $R_2$ is H and $R_1$ is

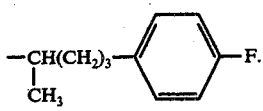

4. A compound according to claim 1, wherein $R_2$ is —$COCH_3$ and $R_1$ is

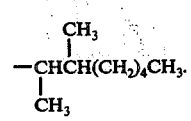

5. A compound according to claim 1, wherein $R_2$ is —$SO_2CH_3$ and $R_1$ is

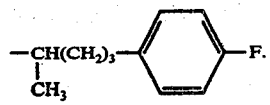

6. A compound according to claim 1, wherein $R_2$ is

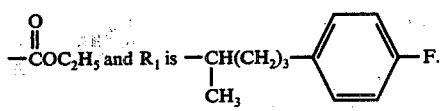

7. A compound according to claim 1, wherein $R_2$ is —$CONH_2$ and $R_1$ is

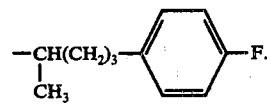

8. A compound according to claim 1, wherein $R_2$ is

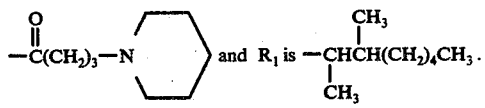

9. A compound according to claim 1, wherein $R_2$ is

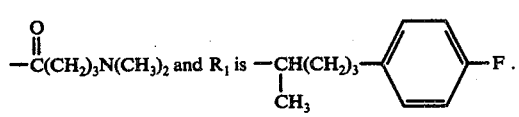

* * * * *